(12) United States Patent
Zuber et al.

(10) Patent No.: US 12,161,796 B2
(45) Date of Patent: Dec. 10, 2024

(54) PIERCING ACCESSORY FOR INHALER ARTICLE AND SYSTEM

(71) Applicant: PHILIP MORRIS PRODUCTS S.A., Neuchâtel (CH)

(72) Inventors: Gérard Zuber, Neuchaâtel (CH); Judith Waller, Ostersund (SE); Masja Bertien Mooij, Rotterdam (NL)

(73) Assignee: PHILIP MORRIS PRODUCTS, S.A., Neuchâtel (CH)

( * ) Notice: Subject to any disclaimer, the term of this patent is extended or adjusted under 35 U.S.C. 154(b) by 0 days.

(21) Appl. No.: 16/758,111

(22) PCT Filed: Oct. 22, 2018

(86) PCT No.: PCT/IB2018/058209
§ 371 (c)(1),
(2) Date: Apr. 22, 2020

(87) PCT Pub. No.: WO2019/082057
PCT Pub. Date: May 2, 2019

(65) Prior Publication Data
US 2020/0275710 A1  Sep. 3, 2020

(30) Foreign Application Priority Data
Oct. 25, 2017  (EP) .................................... 17198362

(51) Int. Cl.
*A61M 15/00* (2006.01)
*A24B 15/16* (2020.01)
(Continued)

(52) U.S. Cl.
CPC ......... *A61M 15/0035* (2014.02); *A24F 42/20* (2020.01); *A24F 42/60* (2020.01);
(Continued)

(58) Field of Classification Search
None
See application file for complete search history.

(56) References Cited

U.S. PATENT DOCUMENTS

| | | |
|---|---|---|
| 4,338,931 A | 7/1982 | Cavazza |
| 6,257,231 B1 | 7/2001 | Shick et al. |

(Continued)

FOREIGN PATENT DOCUMENTS

| | | |
|---|---|---|
| CN | 105072936 | 11/2015 |
| CN | 106455726 | 2/2017 |

(Continued)

OTHER PUBLICATIONS

Extended EP Search Report for EP 21200315.6 issued by the European Patent Office dated Jan. 4, 2022; 15 pgs.

(Continued)

*Primary Examiner* — Phu H Nguyen
(74) *Attorney, Agent, or Firm* — Mueting Raasch Group

(57) ABSTRACT

An inhaler system includes an inhaler article and a piercing article. The piercing article contains a recessed piercing element and is configured to receive a distal end of the inhaler article. The piercing element pierces or punctures a single hole into a capsule contained within the inhaler article when the inhaler article is seated into the piercing article.

20 Claims, 2 Drawing Sheets

Figure 1:
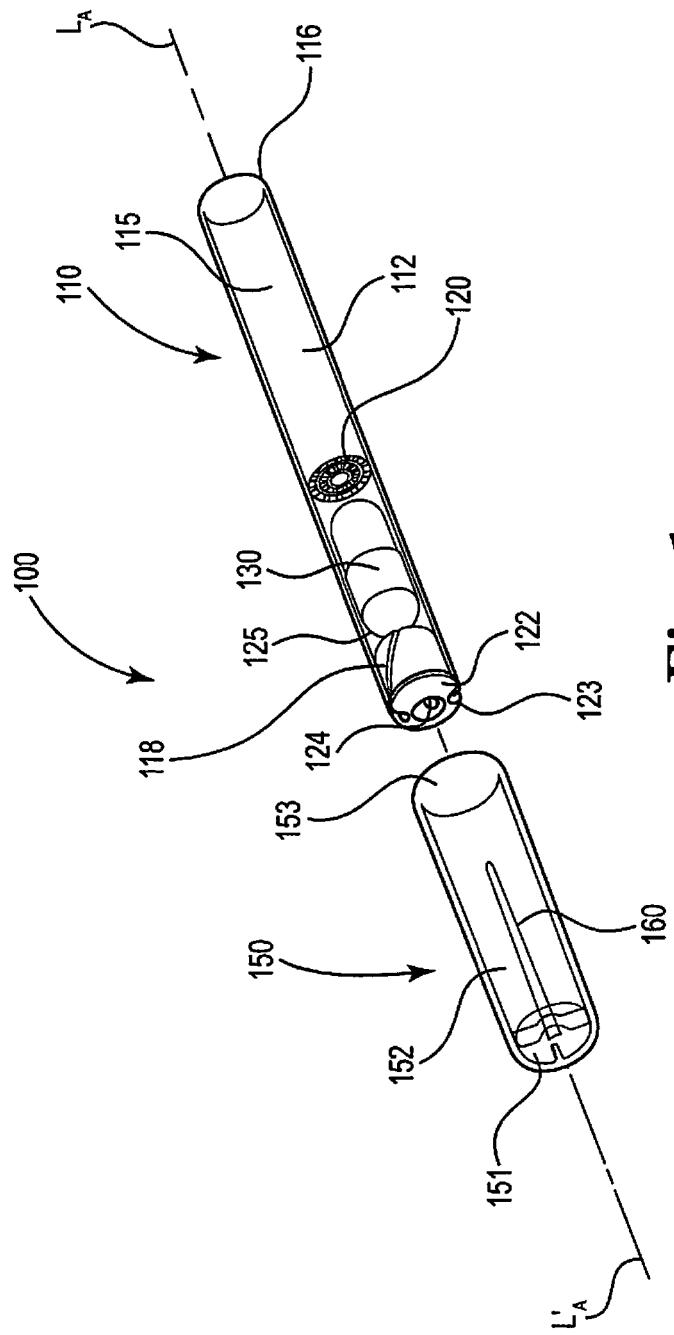

(51) Int. Cl.
*A24B 15/18* (2006.01)
*A24F 42/20* (2020.01)
*A24F 42/60* (2020.01)

(52) U.S. Cl.
CPC ...... *A61M 15/0021* (2014.02); *A61M 15/004* (2014.02); *A24B 15/16* (2013.01); *A24B 15/186* (2013.01); *A61M 2202/064* (2013.01)

(56) References Cited

U.S. PATENT DOCUMENTS

| | | | |
|---|---|---|---|
| 9,010,323 | B2 | 4/2015 | Haerder et al. |
| 9,980,521 | B2 | 5/2018 | Buehler et al. |
| 9,986,766 | B2 | 6/2018 | Batista |
| 10,028,531 | B2 | 7/2018 | Clements et al. |
| 2009/0260623 | A1 | 10/2009 | Dunkley et al. |
| 2015/0231344 | A1 | 8/2015 | Deboeck et al. |
| 2016/0029694 | A1 | 2/2016 | Clements et al. |
| 2016/0199598 | A1* | 7/2016 | Curtis ............... A61M 15/003 128/203.15 |
| 2016/0227839 | A1 | 8/2016 | Zuber |
| 2016/0354563 | A1 | 12/2016 | Pfrang et al. |
| 2017/0042244 | A1 | 2/2017 | Buehler et al. |
| 2017/0143039 | A1 | 5/2017 | Batista |
| 2018/0369517 | A1* | 12/2018 | Zuber ..................... A24F 42/60 |

FOREIGN PATENT DOCUMENTS

| | | |
|---|---|---|
| CN | 106535677 | 3/2017 |
| EP | 0079478 A1 | 5/1983 |
| EP | 0388621 B1 | 8/1992 |
| GB | 1396258 | 6/1975 |
| RU | 2474438 C2 | 2/2013 |
| WO | WO 91/18636 A1 | 12/1991 |
| WO | WO 98/26828 A2 | 6/1998 |
| WO | WO 2002/083220 A2 | 10/2002 |
| WO | 20090007352 | 1/2009 |
| WO | WO 2012/155058 A1 | 11/2012 |
| WO | WO 2013/008038 A2 | 1/2013 |
| WO | 20140140087 | 9/2014 |
| WO | 20150101651 | 7/2015 |
| WO | WO 2015/166350 A2 | 11/2015 |
| WO | WO 2015/193498 A1 | 12/2015 |
| WO | WO 2017/079397 A1 | 5/2017 |
| WO | WO 2017/109678 A1 | 6/2017 |
| WO | WO-2017109626 A1 * | 6/2017 ............. A24F 40/20 |
| WO | WO 2018/007886 A1 | 1/2018 |
| WO | WO 2018/036836 A2 | 3/2018 |

OTHER PUBLICATIONS

International Search Report and Written Opinion issued by the European Patent Office for PCT/IB2018/058208; dated Feb. 4, 2019; 15 pgs.
Extended EP Search Report issued by the European Patent Office for EP 17198367.9, dated Apr. 19, 2018; 9 pgs.
Cohen et al., "GRAS Flavoring Substances," 27. *GRAS Flavoring Substances. Food Technology for Flavoring Extract Manufacturers Association,* Aug. 2015:69(8):40-59.
Hall, R.L. & Oser, B.L., "Recent Progress in the Consideration of Flavoring Ingredients under the Food Additive Amendments 3. GRAS substances," *Food Technology,* Feb. 1965: p. 151-197.
Russian Office Action for RU Application No. 2020114638 issued by the Patent Office of the Russian Federation dated Feb. 22, 2022; 19 pgs. including English Translation.
Extended European Search Report issued by the European Patent Office for EP 17198362.0, dated Apr. 12, 2018; 8 pgs.
International Search Report and Written Opinion for PCT/IB2018/058209; issued by the European Patent Office dated Jan. 3, 2019; 16 pgs.
International Preliminary Report on Patentability issued by the European Patent Office for PCT/IB2018/058209; dated Apr. 10, 2019; 23 pgs.
European Communication under Rule 71(3) EPC Intent to Grant for EP 18799864.6, issued by the European Patent Office, dated Jun. 1, 2021; 7 pgs.
Chinese Office Action for CN 201880064252.7 issued by the Chinese Patent Office dated Sep. 28, 2021; 12 pgs. including English translation.

* cited by examiner

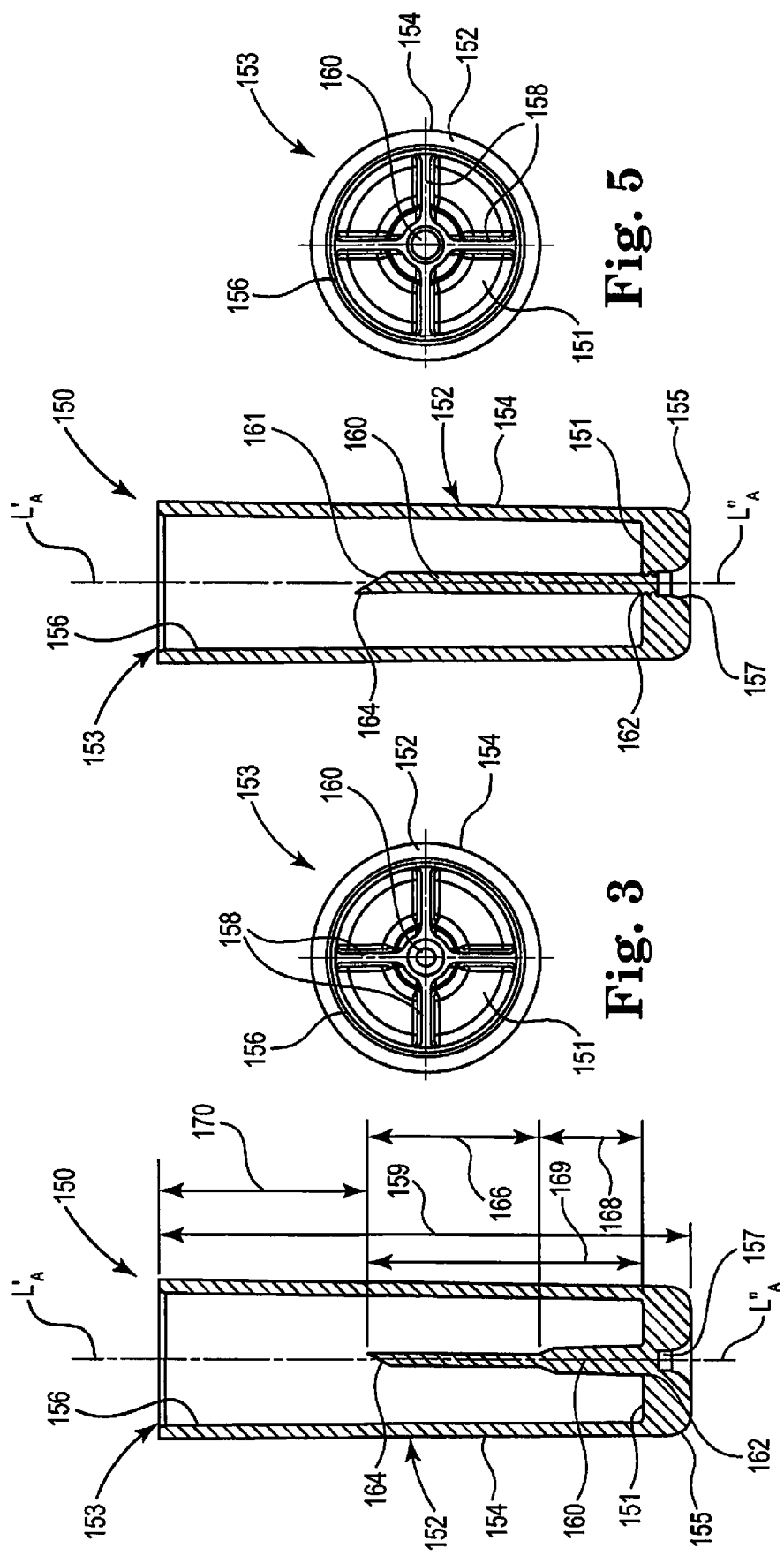

PIERCING ACCESSORY FOR INHALER ARTICLE AND SYSTEM

This application is the § 371 U.S. National Stage of International Application No. PCT/IB2018/058209, filed 22 Oct. 2018, which claims the benefit of European Application No. 17198362.0, filed 25 Oct. 2017, the disclosures of which are incorporated by reference herein in their entireties.

This disclosure relates to a piercing accessory for an inhaler article and inhaler systems that include the piercing accessory and inhaler article.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

It would be desirable to provide an inhaler system that minimizes moving parts. It would be desirable that this piercing accessory have a protected piercing end. It would be desirable to provide an inhaler system with a reusable piercing accessory. It would be desirable to provide an inhaler system that includes a low-profile and reusable piercing accessory.

It would be desirable to provide a nicotine powder inhaler that provides nicotine particles to the lungs at inhalation or air flow rates that are within conventional smoking regime inhalation or air flow rates. It would also be desirable to provide deliver the nicotine powder with an inhaler article that has a form similar to a conventional cigarette. It would also be desirable to provide an inhaler article that is simple to manufacture and convenient to use by a consumer.

This disclosure is directed to an inhaler system that includes an inhaler article and a piercing article. The piercing article contains a recessed piercing element and is configured to receive a distal end of the inhaler article. The piercing element pierces or punctures a single hole into the capsule contained within the inhaler article when the inhaler article is seated into the piercing article. The inhaler article is separated from the piercing article and then utilized by a consumer. The piercing article may be re-utilized on subsequent inhaler articles. The piercing article preferably defines a cylindrical body.

The inhaler article includes a body defining an inhaler outer surface. The body extending along an inhaler longitudinal axis from mouthpiece end to a distal end. The body has an inhaler length along a longitudinal axis. The piercing article includes a cylindrical housing defining a cylindrical housing outer surface and a cylindrical housing inner surface. The cylindrical housing extends along a cylindrical housing longitudinal axis from a distal end to an open proximal end, a cylindrical housing length. A piercing element is contained within and fixed to the cylindrical housing or distal end. The piercing element extends along a piercing element longitudinal axis from a fixed distal end to a piercing end a piercing element length. The piercing element is recessed from the open proximal end a recessed distance. The cylindrical housing open proximal end is configured to receive the distal end of the inhaler article.

Advantageously, the inhaler system provides an inhaler system that minimizes moving parts. Advantageously, the inhaler system utilizes a separate piercing accessory. This may enable the piercing accessory to be reusable and the inhaler article to be disposable after a single use. Advantageously, recessing the protected piercing element may facilitate protection of the piercing element and protection for a user from the piercing element. The piercing element may be recessed from the piercing accessory open end by at least 25% of the total length of the piercing accessory.

Advantageously, the inhaler system provides nicotine particles to the lungs at inhalation or air flow rates that are within conventional smoking regime inhalation or air flow rates. The inhaler delivers the nicotine powder with an inhaler article that has a form similar to a conventional cigarette. The inhaler article and boundary element may be formed with a simple manufacturing method.

The piercing article cylindrical housing may have a tapered inner diameter that decreases from the open end to the recessed end. The cylindrical housing inner diameter may taper down in a range from about 3% to about 13%, or in a range from about 5% to about 10%. The piercing article distal end may mate with the inhaler article distal end, when the inhaler article is received within the piercing article.

Advantageously, the tapered inner diameter may provide a guided alignment of the piercing element to accurately puncture the capsule within the inhaler article. The tapered inner diameter may provide a reliable hard stop or interference fit with the outer surface of the inhaler article when the inhaler article is fully seated or received within the piercing article. Tapering the inner diameter of the cylindrical housing may facilitate locating the piercing accessory on the distal end of the inhaler article.

The piercing element is preferably formed of a polymeric material. The polymeric material forming the cylindrical housing may be a different type of polymeric material than the polymeric material forming the piercing element. The cylindrical housing may be formed of a first polymeric material and the piercing element may be formed of a second polymeric material that is different than the first polymeric material.

The piercing article and piercing element may be formed of a polymeric material. The piercing element may be formed of a fibre-reinforced polymeric material. The polymeric or fibre-reinforced polymeric piercing element may have first diameter adjacent the piercing end and a second diameter near the fixed distal end, the second diameter being greater than the first diameter. In one example, the piercing element may be formed of a fibre-reinforced polymeric material and the piercing article cylindrical housing is formed of a polymeric material that is free of fibres.

Advantageously, a polymeric or fibre-reinforced polymeric piercing element may be easily formed with the polymeric piercing article cylindrical housing and may be simply bonded or fixed to one another. Advantageously, the piercing article is a separate component from the inhaler article.

The inhaler system described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler may have a form similar to a conventional cigarette and may mimic the ritual of conventional smoking. This inhaler may be simple to manufacture and convenient to use by a consumer.

Air flow management through the capsule cavity may cause the capsule to rotate during inhalation and consumption. The capsule may contain particles containing nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The piercing article described herein may be combined with an inhaler article containing a capsule for activating the inhaler article by piercing the capsule, releasing the particles contained inside the capsule and enabling the article to deliver the particles to a consumer. The piercing article is separate from the inhaler article. The piercing article is not couple to or form any portion of the inhaler article. Advantageously, the piercing article does not form a portion of the inhaler article and defines a low-profile. A plurality of these inhaler articles may be combined with a piercing article to form a kit. A single piercing element may be utilized on 10 or more, or 25 or more, or 50 or more, or 100 or more, inhaler articles to activate (puncture or pierce) a capsule contained within each inhaler article.

An inhaler article includes a body extending along a longitudinal axis from a mouthpiece end to a distal end. The body has an inhaler length extending between the mouthpiece end to the distal end. The body defines an inhaler outer surface. A capsule cavity is defined within the body and extends along the longitudinal axis. A mouthpiece air channel extends from the capsule cavity to the mouthpiece end. A boundary element is between the capsule cavity and the mouthpiece air channel. The boundary element includes apertures fluidly connecting the capsule cavity with the mouthpiece air channel. The distal end may include an end cap or endpiece element.

The piercing article includes a cylindrical housing. The cylindrical housing defines a cylindrical housing outer surface and a cylindrical housing inner surface. The piercing article is defined by a cylindrical outer housing. The cylindrical housing extends along a cylindrical housing longitudinal axis from a distal end to an open proximal end, a cylindrical housing length. The cylindrical housing open proximal end is configured to receive the distal end of the inhaler article. The distal end may be a restricted. For example, the restricted distal end may have a diameter that is smaller than the diameter of the open proximal end. For example, the restricted distal end may be substantially closed and define a closed distal end.

A piercing element is contained within and fixed to the cylindrical housing or distal end. The piercing element extends along a piercing element longitudinal axis from a fixed distal end to a piercing end a piercing element length. The piercing element is recessed from the open proximal end a recessed distance.

Recessing the piercing element into the cylindrical housing protects the piercing element from coming into contact with surfaces not intended to be received within the piercing element. Recessing the piercing element into the cylindrical housing may also protect the piercing element from being damaged or modified by surfaces not intended to be received within the piercing element.

The piercing element may be recessed from the open proximal end by any suitable recessed distance. For example, the piercing element may be recessed from the open proximal end a recessed distance of at least about 10%, at least about 20%, at least about 25%, or at least about 30%, or at least about 35%, or at least about 40%, of the cylindrical housing length. The piercing element may be recessed from the open proximal end a recessed distance of in a range from about 5% to about 50%, or from about 10% to about 40%, or from about 15% to about 40%, or about 20% to about 40%, of the cylindrical housing length.

The piercing element length may be any suitable length relative to the cylindrical housing length. For example, the piercing element length may be about 30% to about 70%, or about 40% to about 60%, of the cylindrical housing length. A distal end of the piercing element may be fixed to the distal end adjacent to or at the distal end of the cylindrical housing. Where the distal end is closed and comprises a distal end wall, the piercing element may be fixed to the distal end wall. The piercing element entire length may be coextensive within the cylindrical housing length.

The fixed distal end of the piercing element may be fixed to the cylindrical housing or distal end by direct bonding. The closed distal end of the piercing article may define an endcap that seals the distal end of the cylindrical housing. The closed distal end may include a recessed portion that recesses into the closed distal end from the outer surface. The recessed portion may be coaxial with the piercing element longitudinal axis. The outer perimeter of the closed distal end may form a smooth rounded edge joining the cylindrical housing outer surface with the closed distal end. The closed distal end may include two or more reinforcing ribs or struts connecting the cylindrical housing inner surface with the piercing element fixed distal end. The cylindrical housing inner surface adjacent to the closed distal end may be configured to mate with the distal end of the inhaler article to provide a mating or seating fit.

The fixed distal end of the piercing element may be fixed to the cylindrical housing or distal end by direct bonding with a distal end of the piercing article. A distal end may have one or more openings defined through the distal end. The distal end may include a recessed portion that recesses into the distal end from the outer surface. The recessed portion may be coaxial with the piercing element longitudinal axis. The outer perimeter of the distal end may form a smooth rounded edge joining the cylindrical housing outer surface with the distal end. The distal end may include two or more reinforcing ribs or struts connecting the cylindrical housing inner surface with the piercing element fixed distal end. The cylindrical housing inner surface adjacent to the distal end may be configured to mate with the distal end of the inhaler article to provide a mating or seating fit.

The cylindrical housing inner surface has an open proximal end diameter and a distal end diameter. The distal end diameter may be less than the open proximal end diameter. The cylindrical housing inner surface diameter may taper down from the open proximal end diameter to the distal end diameter. The cylindrical housing inner surface diameter may taper down by any suitable amount. For example, the cylindrical housing inner surface diameter may taper down in a range from about 3% to about 13%, or about 5% to about 10% of the cylindrical housing inner diameter at the proximal end.

The piercing article has a cylindrical housing outer surface diameter. The cylindrical housing outer surface diameter may be a uniform diameter along the cylindrical housing length. The cylindrical housing outer surface diameter may vary by less than about 2%. The cylindrical housing outer surface may be configured to closely mimic the outer surface of the inhaler article, to provide a low-profile piercing article. The cylindrical housing outer surface may have a smooth cylinder shape similar to the outer surface of the inhaler article. The inhaler surface outer diameter may be any suitable diameter. For example, the inhaler outer surface diameter may be less than about 150%, or less than about 140%, of a diameter of the outer inhaler surface.

The piercing element is formed of a rigid material. The rigid material is sufficiently rigid to pierce, puncture or activate a capsule contained within the inhaler article. The piercing element may be formed of a metal. The piercing element may be formed of stainless steel, such as 316 stainless steel, for example. The piercing element may be formed of a polymeric material. The piercing element may be formed of a fibre-reinforced polymeric material.

Polymeric materials useful for forming the piercing element include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyetheretherketone, or liquid crystal polymer, for example. Polycarbonate or liquid crystal polymer are preferred materials for forming the piercing element.

The polymeric material may be fibre-reinforced and include a plurality of fibres forming a fibre dispersion throughout the piercing element. Fibres forming this fibre dispersion may have an average length of less than about 1 mm, or in a range from about 0.1 mm to about 1 mm, and an average diameter of less than 50 micrometers. The fibres forming the fibre dispersion may be formed of glass, carbon, basalt, graphite, DuPont Kevlar brand aramid fibres, ceramics, natural fibres, polymeric fibres, and metal, for example. Preferably fibres forming the fibre dispersion are composed of glass fibres. The fibre dispersion when present in the polymeric material forming the piercing element may range from about 5% to about 60% by weight, or from about 10% to about 50% by weight, or from about 20% to about 45% by weight, or from about 30% to about 40% by weight. Fibre-reinforced polycarbonate or fibre-reinforced liquid crystal polymer are preferred materials for forming the piercing element.

The cylindrical housing may be formed of any rigid material. The cylindrical housing may be formed of a polymeric material. Polymeric materials useful for forming the cylindrical housing include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyetheretherketone, or liquid crystal polymer, for example. Polyproplyene, polyethylene or co-polymers thereof are preferred materials for forming the cylindrical housing.

The polymeric material forming the cylindrical housing may be a different type of polymeric material than the polymeric material forming the piercing element. The polymeric material forming the cylindrical housing may be free of fibres and the polymeric material forming the piercing element may be a fibre-reinforced polymeric material. In one example, the polymeric material forming the cylindrical housing may be polyproplyene, polyethylene or co-polymers thereof, and the polymeric material forming the piercing element may be fibre-reinforced polycarbonate, liquid crystal polymer, or fibre-reinforced liquid crystal polymer.

The piercing element may define two or more diameters. The piercing element may have a first diameter adjacent the piercing end and a second diameter being greater than the first diameter adjacent to the fixed distal end. The piercing element may have a first length segment adjacent the piercing end and a second length segment adjacent to the fixed distal end. The first length segment may have a substantially constant or uniform diameter. The second length segment may have a substantially constant or uniform diameter, or the second length segment may have a tapering diameter decreasing from the fixed distal end to the first length segment.

The inhaler article may be received into the piercing article such that the inhaler article outer surface and the piercing article cylindrical housing outer surface are concentric. The piercing element longitudinal axis may be coaxial with the cylindrical housing longitudinal axis, and the inhaler longitudinal axis, when the inhaler article is received within the piercing article. At least about 80%, or at least about 90% of the cylindrical housing length may be coextensive with the inhaler length, when the inhaler article is received within the piercing article.

The piercing article may be formed by insertion moulding techniques. The piercing element may first be formed by moulding, for example, and then the cylindrical housing may be moulded around the piercing element bonding to the piercing element. The piercing element may be a metal piercing element, the cylindrical housing may be moulded around the metal piercing element fixing the metal piercing element to the cylindrical housing. A metal piercing element may include protrusions or recesses at the distal end of the piercing element to increase surface area of the distal end of the piercing element and improve fixation within the cylindrical housing moulded material.

An inhaler article air channel may extend through the end cap or endpiece element to provide airflow through the inhaler article. The air channel supplying airflow to the capsule cavity may be configured to induce a swirling air flow pattern within the capsule cavity of the inhaler body. The air channel configuration may induce rotational air flow or swirling air flow as the air flows through the air channel and through the capsule cavity. Air flow through the inhaler device may enter the inhaler device at the distal end of the inhaler device and moves along the longitudinal axis of the inhaler device to the mouthpiece end. Air flow through the inhaler device may enter the inhaler device along the inhaler body upstream or along the capsule cavity and move along the longitudinal axis of the inhaler device to the mouthpiece end.

The inhaler article end cap or endpiece element may include a linear piercing channel extending through the length of the end cap or end piece element. The linear piercing channel may extend along a central axis of the end cap or end piece element. The linear piercing channel may be co-axial with the longitudinal axis of the inhaler body. The linear piercing channel may be sized to allow a piercing element to pass through the linear piercing channel. The end cap or endpiece element may define a resealable element disposed along or within the linear piercing channel. The resealable element may seal the linear piercing channel. The resealable element may form an airtight seal or barrier along the linear piercing channel, when a piercing element is not within the resealable element. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element.

Resealable elements or membranes may be formed of elastic material such as rubber, silicone, metal foil co-laminated with a polymer, or latex and the like, or cellulose acetate tow, such as high-density cellulose acetate tow.

The inhaler body may resemble a smoking article or cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 6 mm to about 10 mm, or from about 7 mm to about 10 mm, or about 7 mm to about 9 mm, or about 7 mm to about 8 mm or about 8 mm. The inhaler body may have a length (along the longitudinal axis) in a range from about 40 mm to about 90 mm, or from about 50 mm to about 80 mm, or about 50 mm to about 70 mm, or 55 mm.

The capsule cavity may define a cylindrical space configured to contain a capsule (that may have an obround shape or a circular cross-section, for example). The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized to contain a obround capsule. The capsule cavity may have a substantially cylindrical or cylindrical cross-section along the length of the capsule cavity. The capsule cavity may have a uniform inner diameter. The capsule may have an outer diameter that is about 85% to about 95% of the inner diameter of the capsule cavity. The configuration of the capsule cavity relative to the capsule may promote limited movement of the capsule during activation or piercing of the capsule.

The configuration of the capsule cavity relative to the capsule may promote the capsule to rotate with stability within the capsule cavity. The longitudinal axis of the capsule may rotate with stability co-axially with the longitudinal axis of the inhaler body during inhalation.

Stable rotation refers to the longitudinal axis of the inhaler body being substantially parallel or co-axial with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule may be sealed within the inhaler article prior to consumption. The inhaler article may be contained within a sealed or airtight container or bag. The inhaler article may include one or more peelable or removable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

The separate piercing article, described, forms a single aperture through the capsule received in the capsule cavity. The piercing article piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 5 micrometers or less, or in a range from about 1 micrometer to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a transparent perspective view of an illustrative inhaler system.

FIG. 2 is a cross-sectional schematic diagram of an illustrative piercing accessory.

FIG. 3 is a top view schematic diagram of the open end of the piercing accessory illustrated in FIG. 2.

FIG. 4 is a cross-sectional schematic diagram of another illustrative piercing accessory.

FIG. 5 is a top view schematic diagram of the open end of the piercing accessory illustrated in FIG. 4.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 illustrates a transparent perspective view an exemplary inhaler system 100. The inhaler system 100 includes an inhaler article 110 and a separate piercing article 150. The inhaler article 110 may be received within the piercing article 150 to activate or pierce a capsule 130 disposed within the inhaler article 110. The inhaler article 110 is withdrawn from the piercing article 150 prior to use by the consumer.

The inhaler article 110 includes a body 112 extending along a longitudinal axis $L_A$ from a mouthpiece end 116 to a distal end 118 and a capsule cavity 125 defined within the body 112. The body 112 may have a uniform diameter of about 7.5 mm and a length of about 55 mm. The body 112 may have a uniform diameter inner diameter of about 6.5 mm. The body 112 may have a uniform thickness about 1 mm. A mouthpiece air channel 115 extends from the capsule cavity 125 to the mouthpiece end 116. An end cap or end element 122 is disposed within the distal end 118 and extends to the capsule cavity 125. The end cap or end element 122 includes an air channel 123 extending along the end cap or end element 122. The air channel 123 creates a swirling airflow through the capsule cavity 125. The end cap or end element 122 and a boundary element 120 bound the capsule cavity 125. A capsule 130 is disposed within the capsule cavity 125. The capsule 130 contains particles comprising nicotine. The end cap or end element 122 and the boundary element 120 cooperate to contain the capsule 130 longitudinally within the capsule cavity 125. The capsule 130 axis of rotation may be coextensive with the longitudinal axis $L_A$.

The inhaler article end cap or end element 120 may include a linear piercing channel 124 extending through the length of the end cap or end element 120. The linear piercing channel 124 may be co-axial with the longitudinal axis $L_A$ of the inhaler body 112. The linear piercing channel 124 may be sized to allow a piercing element 160 to pass through the linear piercing channel 124. The end cap or end element 120 may define a resealable element disposed along or within the linear piercing channel 124. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

FIG. 2 is a cross-sectional schematic diagram of the illustrative piercing article or accessory 150. FIG. 3 is a top view schematic diagram looking into the open end 153 of the piercing article or accessory 150 illustrated in FIG. 2. FIG. 4 is a cross-sectional schematic diagram of another illustrative piercing article or accessory 150. FIG. 5 is a top view schematic diagram looking into the open end 153 of the piercing accessory illustrated in FIG. 4.

The piercing article 150 includes a cylindrical housing 152 defining a cylindrical housing outer surface 154 and a cylindrical housing inner surface 156. The cylindrical housing extends along a cylindrical housing longitudinal axis $L_A'$ from a distal end 151 to an open proximal end 153, a cylindrical housing length 159 that may be about 33 mm. The distal end 151 is illustrated as a closed end cap. The cylindrical housing open proximal end 153 is configured to receive the distal end 118 of the inhaler article 110. A piercing element 160 is contained within and fixed to the cylindrical housing 152 or distal end 151. The piercing element 160 extends along a piercing element longitudinal axis $L_A''$ from a fixed distal end 162 to a piercing end 164 a piercing element length 169 that may be about 17 mm or about 18 mm. The piercing element 160 is recessed from the open proximal end 153 a recessed distance 170 that may be about 12 mm or about 13 mm. The piercing element 160 has a cutting surface 161 at the piercing end 164, the cutting surface may be a planar surface forming an angle of about 30 degrees with the piercing element longitudinal axis $L_A''$.

FIG. 2 and FIG. 3 illustrate a piercing element 160 having two different diameters. The piercing element 130 has a first length segment 166 adjacent the piercing end and a second length segment 168 adjacent to the fixed distal end 162. The first length segment 166 may have a substantially constant or uniform diameter. The first length segment may have a diameter of about 0.8 mm and a length of about 11 mm or about 12 mm. The second length segment 168 may have a substantially constant or uniform diameter that is greater than the first length segment 166 diameter, or the second length segment 168 may have a tapering diameter (as shown) decreasing from the fixed distal end 162 to the first length segment 166. FIG. 4 and FIG. 5 illustrate a piercing element 160 having a constant or uniform diameter. The second length segment 168 may have an initial diameter of about 1.8 mm and a final diameter of about 1.5 mm and a length of about 6 mm or about 7 mm.

The piercing article 150 cylindrical housing 152 cylindrical housing inner surface 156 has an open proximal end 153 diameter and a distal end 151 diameter that is less than the open proximal end 153 diameter. This cylindrical housing inner surface 156 diameter tapers down from the open proximal end diameter 153 to the distal end 151 diameter. The cylindrical housing outer surface 154 diameter may be constant at about 9.8 mm and the cylindrical housing inner surface 156 diameter may be about 8.4 mm at the open proximal end 153, and about 7.7 mm at the distal end 151.

The fixed distal end 162 of the piercing element 160 is fixed to the distal end by direct bonding with the closed distal end 151 of the piercing article 150. The closed distal end 151 of the piercing article 150 may define an endcap that seals the distal end of the cylindrical housing 152. The closed distal end 151 may include a recessed portion 157 that recesses into the closed distal end 151 from the outer surface. The recessed portion 151 may be coaxial with the piercing element 160 longitudinal axis $L_A''$. The outer perimeter 155 of the closed distal end 151 may form a smooth rounded edge joining the cylindrical housing outer surface 154 with the closed distal end 151.

FIG. 4 and FIG. 5 illustrate a piercing element 160 having a uniform diameter. The piercing element 130 has a length segment extending from the piercing end 164 to the fixed distal end 162. The length segment may have a length of about 17 mm or about 18 mm. The uniform diameter of the piercing element 160 may be about 1.2 mm. The piercing element 160 may be a metal piercing element 160. The fixed distal end 162 includes a surface comprising recesses to allow the material forming the distal end 151 of the cylindrical housing 152 to form an intimate bond with the piercing element 160 fixed distal end 162. The piercing element 160 may be pushed into place through the material forming the distal end 151 of the cylindrical housing 152 during assembly of the piercing article 150. Alternatively, the piercing element 160 may be placed in a mold and material forming the distal end 151 of the cylindrical housing 152 is molded around the piercing element 160 fixed distal end 162 during assembly of the piercing article 150.

The fixed distal end 162 of the piercing element 160 is fixed to the distal end by direct or mechanical fixation with the closed distal end 151 of the piercing article 150. The closed distal end 151 of the piercing article 150 may define an endcap that seals the distal end of the cylindrical housing 152. The closed distal end 151 may include a recessed portion 157 that recesses into the closed distal end 151 from the outer surface. The recessed portion 151 may be coaxial with the piercing element 160 longitudinal axis $L_A''$. The recessed portion 151 may be defined by a distal end portion of the fixed distal end 162 of the piercing element 160. A bottom planar portion of the recessed portion 151 may be defined by a distal end portion of the fixed distal end 162 of the piercing element 160. The outer perimeter 155 of the closed distal end 151 may form a smooth rounded edge joining the cylindrical housing outer surface 154 with the closed distal end 151.

The piercing article 150 cylindrical housing 152 cylindrical housing inner surface 156 has an open proximal end 153 diameter and a distal end 151 diameter that is less than the open proximal end 153 diameter. This cylindrical housing inner surface 156 diameter tapers down from the open proximal end diameter 153 to the distal end 151 diameter. The cylindrical housing outer surface 154 diameter may be constant at about 9.8 mm and the cylindrical housing inner surface 156 diameter may be about 8.4 mm at the open proximal end 153, and about 7.7 mm at the distal end 151.

FIG. 3 and FIG. 5 are top view schematic diagrams of the open end of the piercing accessories 150. The piercing element 160 extends out of the page and is surrounded by the cylindrical housing 152. Four reinforcing ribs or struts 158 are contained within the closed distal end 151. The reinforcing ribs or struts 158 connect the cylindrical housing inner surface 156 with the piercing element 160 fixed distal end 162. The cylindrical housing inner surface 156 is adjacent to the closed distal end 151 and may be configured to mate with the distal end 118 of the inhaler article 110 to provide a mating or seating fit. The reinforcing ribs or struts 158 may mate with the distal end 118 of the inhaler article 110 to provide a mating or seating fit.

The invention claimed is:

1. An inhaler system comprising:
    an inhaler article comprising a body defining an inhaler outer surface, the body extending along an inhaler longitudinal axis from mouthpiece end to a distal end an inhaler length; and
    a piercing article comprising:
        a cylindrical housing, defining a cylindrical housing outer surface and a cylindrical housing inner surface, the cylindrical housing extending along a cylindrical housing longitudinal axis from a distal end to an open proximal end a cylindrical housing length, the cylindrical housing open proximal end is configured to receive the distal end of the inhaler article; and
        a piercing element contained within and fixed to the cylindrical housing or distal end, the piercing element extending along a piercing element longitudinal axis from a fixed distal end to a piercing end a piercing element length, the piercing element is recessed from the open proximal end a recessed distance;
    wherein the cylindrical housing inner surface has an open proximal end diameter and a distal end diameter being less than the open proximal end diameter; and
    wherein the cylindrical housing inner surface diameter tapers down from the open proximal end diameter to the distal end diameter.

2. The inhaler system according to claim 1, wherein the piercing element is recessed from the open proximal end a recessed distance of at least about 25% of the cylindrical housing length.

3. The inhaler system according to claim 2, wherein the cylindrical housing inner surface diameter tapers down preferably in a range from 5% to about 10%.

4. The inhaler system according to claim 2, wherein the piercing article has a cylindrical housing outer surface diameter, the cylindrical housing outer surface diameter is a uniform diameter along the cylindrical housing length and is about 150% or less a diameter of the inhaler outer surface.

5. The inhaler system according to claim 1, wherein the cylindrical housing inner surface diameter tapers down preferably in a range from about 3% to about 13%.

6. The inhaler system according to claim 5, wherein the piercing article has a cylindrical housing outer surface diameter, the cylindrical housing outer surface diameter is a uniform diameter along the cylindrical housing length and is about 150% or less a diameter of the inhaler outer surface.

7. The inhaler system according to claim 1, wherein the piercing element is formed of a polymeric material.

8. The inhaler system according to claim 1, wherein the piercing element is formed of a fibre-reinforced polymeric material.

9. The inhaler system according to claim 1, wherein the piercing element is formed of polycarbonate or liquid crystal polymer.

10. The inhaler system according to claim 1, wherein the piercing element is formed of a metal.

11. The inhaler system according to claim 1, wherein the cylindrical housing is formed of a polymeric material.

12. The inhaler system according to claim 11, wherein the piercing article has a cylindrical housing outer surface diameter, the cylindrical housing outer surface diameter is a uniform diameter along the cylindrical housing length and is about 140% or less a diameter of the inhaler outer surface.

13. The inhaler system according to claim 1, wherein the piercing article has a cylindrical housing outer surface diameter, the cylindrical housing outer surface diameter is a uniform diameter along the cylindrical housing length and is about 150% or less a diameter of the inhaler outer surface.

14. The inhaler system according to claim 1, wherein the piercing element longitudinal axis is substantially coaxial with the cylindrical housing longitudinal axis, and the inhaler longitudinal axis, when the inhaler article is received within the piercing article.

15. The inhaler system according to claim 1, wherein the inhaler article distal end mates with the piercing article distal end, when the inhaler article is received within the piercing article.

16. The inhaler system according to claim 1, wherein the piercing element length is about 40% to about 60% of the cylindrical housing length.

17. The inhaler system according to claim 1, wherein the piercing element has a first diameter adjacent the piercing end and a second diameter adjacent to the fixed distal end, the second diameter being greater than the first diameter.

18. The inhaler system according to claim 1, wherein at least about 80% of the cylindrical housing length is coextensive with the inhaler length, when the inhaler article is received within the piercing article.

19. The inhaler system according to claim 1, wherein the cylindrical housing inner surface diameter tapers down preferably in a range from about 5% to about 10%.

20. The inhaler system according to claim 1, wherein at least about 90% of the cylindrical housing length is coextensive with the inhaler length, when the inhaler article is received within the piercing article.

* * * * *